United States Patent [19]
Dev et al.

[11] Patent Number: 5,944,710
[45] Date of Patent: *Aug. 31, 1999

[54] ELECTROPORATION-MEDIATED INTRAVASCULAR DELIVERY

[75] Inventors: Sukhendu B. Dev, San Diego, Calif.; Nagendu B. Dev, Cleveland, Ohio; Gunter A. Hofmann, San Diego, Calif.

[73] Assignee: Genetronics, Inc., San Diego, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/668,725

[22] Filed: Jun. 24, 1996

[51] Int. Cl.⁶ .................................................. A61M 31/00
[52] U.S. Cl. .............................................. 604/500; 604/21
[58] Field of Search ................... 604/19–21, 49, 604/500; 435/173.6; 935/52

[56] References Cited

U.S. PATENT DOCUMENTS

| | | |
|---|---|---|
| 4,081,340 | 3/1978 | Zimmerman et al. . |
| 4,663,292 | 5/1987 | Wong et al. . |
| 4,747,819 | 5/1988 | Phipps et al. . |
| 5,019,034 | 5/1991 | Weaver et al. ............................ 604/20 |
| 5,088,977 | 2/1992 | Sibalis ..................................... 604/20 |
| 5,304,120 | 4/1994 | Crandell et al. . |
| 5,425,703 | 6/1995 | Feiring . |
| 5,498,238 | 3/1996 | Shapland et al. ........................ 604/21 |
| 5,507,724 | 4/1996 | Hofmann et al. ........................ 604/21 |
| 5,554,119 | 9/1996 | Harrison et al. . |
| 5,634,899 | 6/1997 | Shapland et al. ........................ 604/21 |

*Primary Examiner*—Mark Bockelman
*Attorney, Agent, or Firm*—Fish & Richardson P.C.

[57] ABSTRACT

A method for sustained intravascular delivery via electroporation is provided. The method is useful for delivery of therapeutic compositions such as antithrombotic and anticoagulant agents. The invention also provides a catheter apparatus for introducing a composition into at least one cell in a vessel in a subject.

18 Claims, 9 Drawing Sheets

Pulsed artery

Before autofluorescence correction
(2 hrs. after excision)

Non-pulsed artery

Before autofluorescence correction
(2 hrs. after excision)

R1L1: Heparin, no pulse
(left artery)
8 hrs.

R1R1: Heparin, with pulse
(right artery)
8 hrs.

R2L1: Heparin, with pulse
(left artery)
5 hrs.

R2R1: Heparin, no pulse
(right artery)
5 hrs.

4L2: Heparin, with pulse (left artery)

4R2: Heparin, no pulse (right artery)

4L1: Heparin, with pulse (left artery)

1L3: Heparin, no pulse (left artery)

12R1: Heparin, with pulse (right artery)

12L1: Heparin, no pulse (left artery)

ELECTROPORATION-MEDIATED INTRAVASCULAR DELIVERY

FIELD OF THE INVENTION

The present invention relates generally to the field of electroporation and specifically to a method of sustained intravascular delivery of compositions such as antithrombotic and anticoagulant agents.

BACKGROUND OF THE INVENTION

For some time now, it has been known that electric fields could be used to create pores in cells without causing permanent damage to them. This discovery made possible the insertion of large molecules into cell cytoplasm. It is known that genes and other molecules such as pharmacological compounds can be incorporated into live cells through a process known as electroporation.

Treatment of cells by electroporation is carried out by infusing a composition into a patient and applying an electric field to the desired site of treatment between a pair of electrodes. The field strength must be adjusted reasonably accurately so that electroporation of the cells occurs without damage, or at least minimal damage, to any normal or healthy cells. The distance between the electrodes can then be measured and a suitable voltage according to the formula $E=V/d$ can then be applied to the electrodes (E=electric field strength in V/cm; V=voltage in volts; and d=distance in cm).

Studies have also shown that large size nucleotide sequences (up to 630 kb) can be introduced into mammalian cells via electroporation (Eanault, et al., *Gene (Amsterdam)*, 144(2):205, 1994; *Nucleic Acids Research*, 15(3):1311, 1987; Knutson, et al., *Anal. Biochem.*, 164:44, 1987; Gibson, et al., *EMBO J.*, 6(8):2457, 1987; Dower, et al., *Genetic Engineering*, 12:275, 1990; Mozo, et al., *Plant Molecular Biology*, 16:917, 1991), thereby affording an efficient method of gene therapy, for example.

Iontophoresis uses electrical current to activate and to modulate the diffusion of a charged molecule across a biological membrane, such as the skin, in a manner similar to passive diffusion under a concentration gradient, but at a facilitated rate. In general, iontophoresis technology uses an electrical potential or current across a semipermiable barrier. Delivery of heparin molecules to patients has been shown using iontophoresis (IO), a technique which uses low current (d.c.) to drive charged species into the arterial wall. Iontophoretic delivery of heparin (1000 U/ml) into porcine artery was shown to be safe and well tolerated without any change in the coronary angiography or normal physiological parameters such as blood pressure and cardiac rhythm. Although heparin in varying concentration from 1000 U to 20,000 U/ml results in greater concentrations remaining in the vessel after IO delivery compared to passive delivery, approximately 1 hour after the delivery of heparin, 96% of the drug washes out (Mitchel, et al., ACC 44th Annual Scientific Session, Abs.#092684, 1994). It has also been reported that platelet deposition following IO delivery of heparin is reduced in the pig balloon injury model. $^{125}$I-labeled hirudin has also been delivered iontophoretically into porcine carotid artery (Fernandez-Ortiz, et al., *Circulation*, 89:1518, 1994). A local concentration of hirudin can be achieved by IO, however, as with the above experiments with heparin, 80% of the drug washes out in 1 hour and after three hours, the level is the same as for the passive delivery.

Heparins are widely used therapeutically to prevent and treat venous thrombosis. Apart from interactions with plasma components such as antithrombin III or heparin cofactor II, interactions with blood and vascular wall cells may underlie their therapeutic action. The term heparin encompasses to a family of unbranched polysaccharide species consisting of alternating 1→4 linked residues of uronic acid (L-iduronic or D-glucuronic) and D-glucosamine. Crude heparin fractions commonly prepared from bovine and porcine sources are heterogeneous in size (5,000–40,000 daltons), monosaccharide sequence, sulfate position, and anticoagulant activity. Mammalian heparin is synthesized by connective tissue mast cells and stored in granules that can be released to the extracellular space following activation of these cells. Overall, heparin is less abundant than related sulfated polysaccharides, such as heparan sulfate, dermatan sulfate, and chondroitin sulfate, which are synthesized in nearly all tissues of vertebrates. Heparin and these other structures are commonly referred to as glycosaminoglycans.

The anticoagulant activity of heparin derives primarily from a specific pentasaccharide sequence present in about one third of commercial heparin chains purified from porcine intestinal mucosa. This pentasaccharide, -αGlcNR16Sβ(1–4)GlcAα(1–4)GlcNS3S6R2α(1–4)IdoA2Sα(1–4)GlcNS6S where R1=—SO$_3$— or —COCH$_3$ and R2=—H or —SO$_3$—, is a high affinity ligand for the circulating plasma protein, antithrombin (antithrombin III, AT-III), and upon binding induces a conformational change that results in significant enhancement of antithrombin's ability to bind and inactivate coagulation factors, thrombin, Xa, IXa, VIIa, XIa and XIIa. For heparin to promote antithrombin's activity against thrombin, it must contain the specifically recognized pentasaccharide and be at least 18 saccharide units in length. This additional length is believed to be necessary in order to bridge antithrombin and thrombin, thereby optimizing their interaction. Other polymers found in heparin have platelet inhibitory effects or fibrinolytic effects. In clinical development are the low molecular weight heparins (LMW). The heparin compounds contain only the specific polymers required for antithrombin III activation. They have greater specific antithrombotic activity and less antiplatelet activity. They also have the characteristic of being easier to dose and being safer.

A major objective of many biotechnology companies and pharmaceutical industries is to find safe, easy and effective ways of delivering drugs and genes. Specifically, in the area of cardiology, there has been tremendous interest in the delivery of drugs and genes into the arterial wall by a variety of means. Brief reviews have appeared on gene transfer methods related to cardiology (Dzau, et al., *TIBTECH*, 11:205, 1993; Nabel, et al., *TCM*, Jan.-Feb, issue:12, 1991). On the viral front, retroviruses, despite their high efficiency of transfer, have various limitations, such as 1) size (<8 kb), 2) potential for activation of oncogenes, 3) random integration and, 4) inability to transfect non-dividing cells. Other viral vectors such as adenovirus are efficient but have the potential risk of infection and inflammation. HVJ-mediated transfection, although highly efficient, can exhibit non-specific binding. Liposomes, which have become very popular, are safe and easy to work with, but have low efficiency and long incubation times. Recent changes in the formulation of liposomes have, however, has increased their efficiency several fold.

Catheter delivery systems, with many different balloon configurations, have also been used to locally deliver genes and/or drugs. These include: hydrogel balloon, laser-perforated (Wolinsky balloon), 'weeping,' channel and 'Dispatch' balloons and variations thereof (Azrin, et al., Circulation, 90:433, 1994; Consigny, et al., *J Vasc. Interv. Radiol.*, 5:553, 1994; Wolinsky, et al., *JACC*, 17:174B, 1991; Riessen, et al., *JACC*, 23:1234, 1994; Schwartz, Restenosis Summit VII, Cleveland, Ohio, 1995, pp 290–294). Delivery capacity with hydrogel balloon is limited and, during placement, the catheter can lose substantial amount of the drug or agent to be introduced. High pressure jet effect in Wolinsky balloon can cause vessel injury which can be avoided by making many holes, <1 μm, (weeping type). The 'Dispatch' catheter has generated a great deal of interest for drug delivery and it create circular channels and can be used as a perfusion device allowing continuous blood flow.

Gene transfer to endothelium and vascular smooth muscle cells, and site-specific gene expression by retrovirus and liposome have been shown feasible, and cell seeding of vascular prosthesis and stents have also been described (Nabel, et al., *JACC*, 17:189B, 1991; Nabel et al., *Science*, 249:1285, 1990). An ideal method of gene delivery would be intracellular introduction of nucleic acid sequences (e.g., plasmid DNA), locally, to give high level gene expression over a reasonable period of time.

SUMMARY OF THE INVENTION

The present invention provides a method for local and sustained intravascular delivery of a composition in a subject by pulsed electric field, or electroporation. The mode of delivery described herein allows retention of the composition in a vessel in the subject for an extended period of time. The method is a catheter-based system for delivery of therapeutic agents, for example, directly into the cells of the vessel wall. Sustained, high local concentrations of a composition is achieved using the method of the invention.

The method of the invention is useful for intravascular delivery of such compositions as antiproliferative, anticoagulative, antithrombotic, antirestenoitic and antiplatelet agents. The method is useful for cardiologic applications such as treatment of deep-vein thrombosis (DVT), unblocking clogged carotid arteries, peripheral arterial disease and cardiovascular restenosis, for example.

The invention also provides a catheter apparatus for introducing a composition into at least one cell in a vessel in a subject.

DESCRIPTION OF THE PREFERRED EMBODIMENTS

Figure 1:
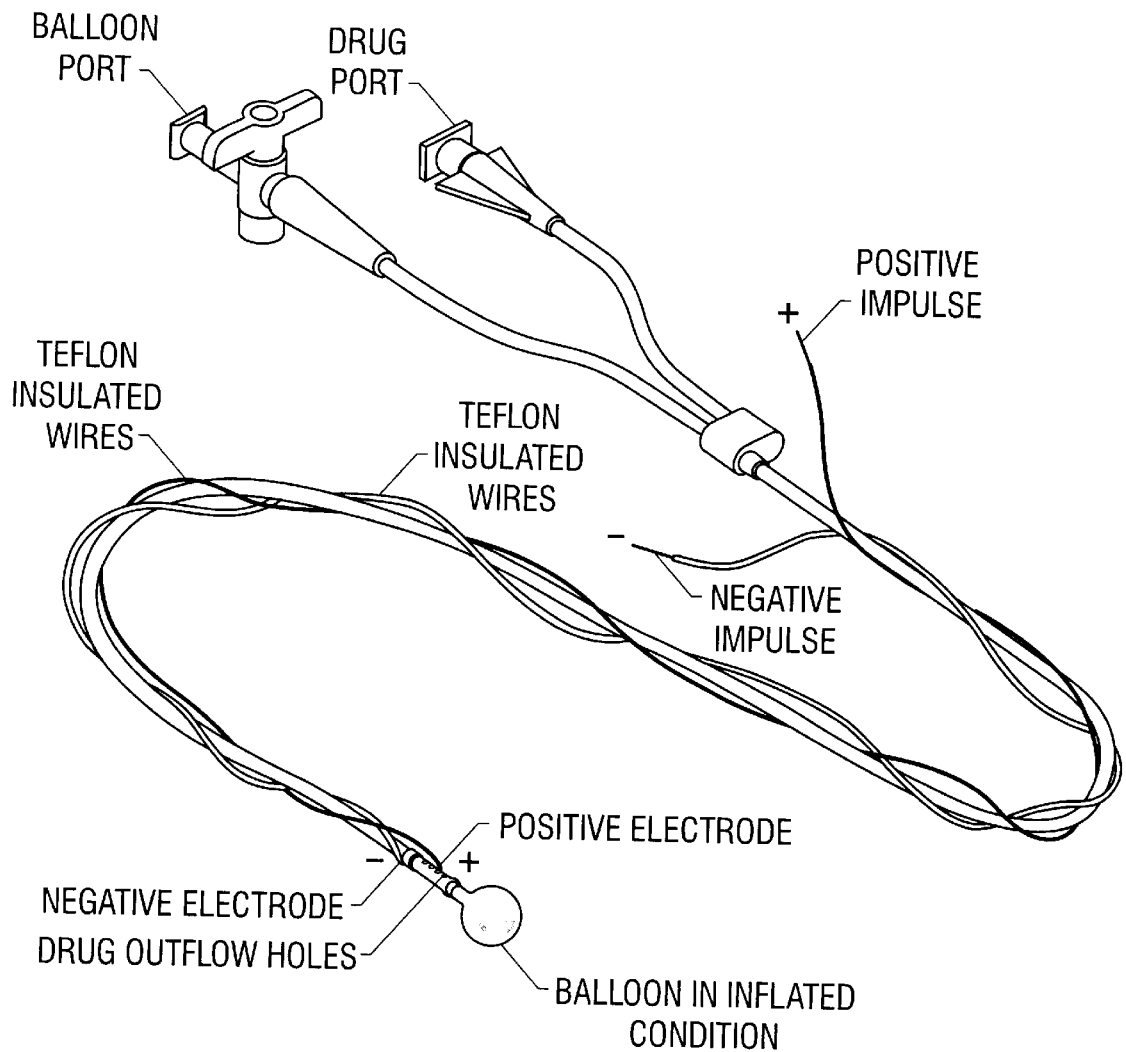
FIG. 1 is a schematic illustration of an endoluminal catheter.
Figure 2A:
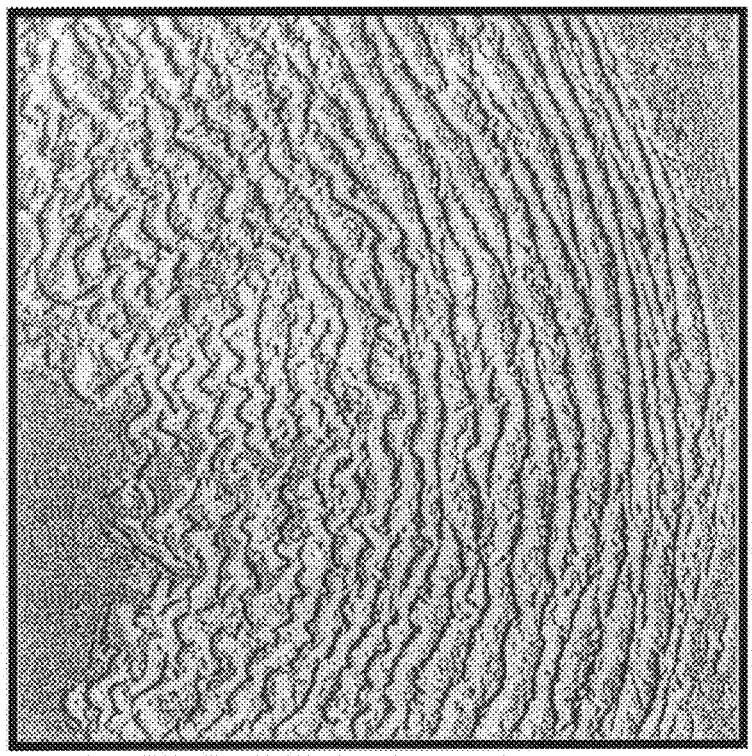
FIG. 2, top, shows a computer image of fluoresceinated heparin in the pulsed rabbit artery, and bottom, in the non-pulsed artery.
Figure 2B:
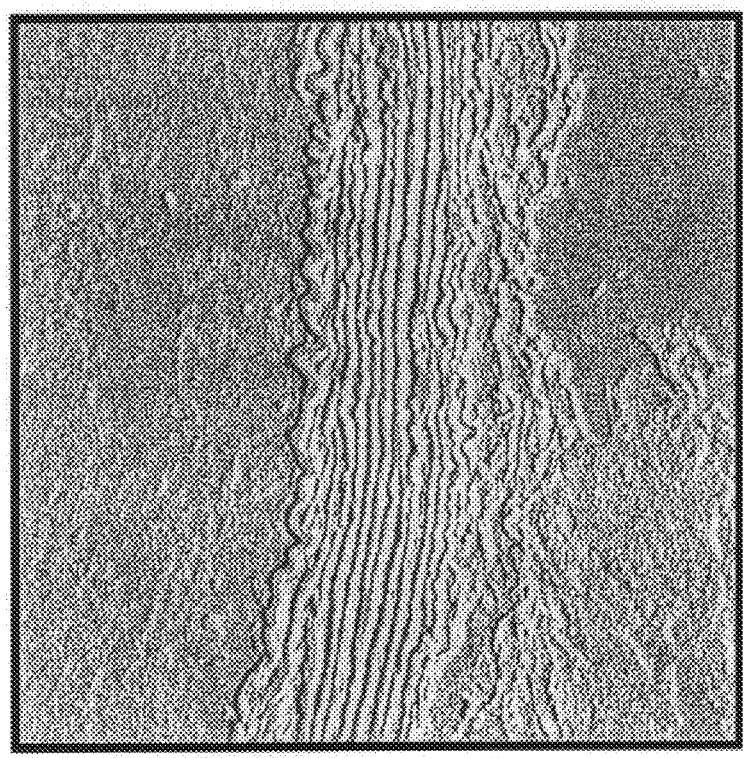
Figure 3A:
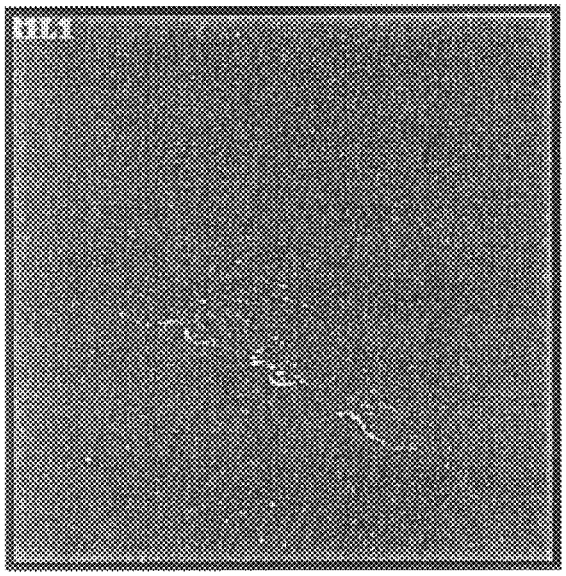
FIG. 3 shows confocal microscopy images of rabbit arteries after fluoresceinated heparin treatment. R1L1 shows the left artery, no pulse; R1R1 shows the right artery, with pulse; R2L1 shows the left artery, with pulse; and R2E1 shows the right artery, no pulse.
Figure 3B:
Figure 3C:
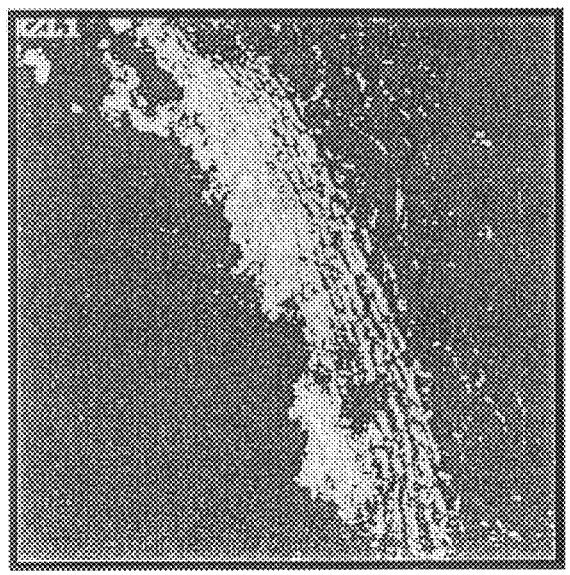
Figure 3D:
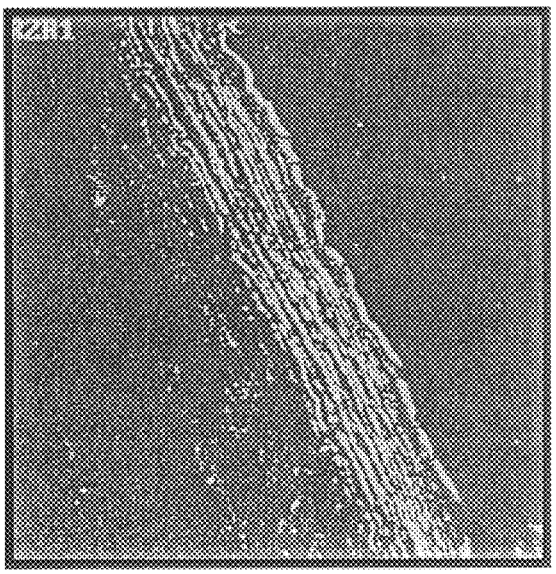
Figure 4A:
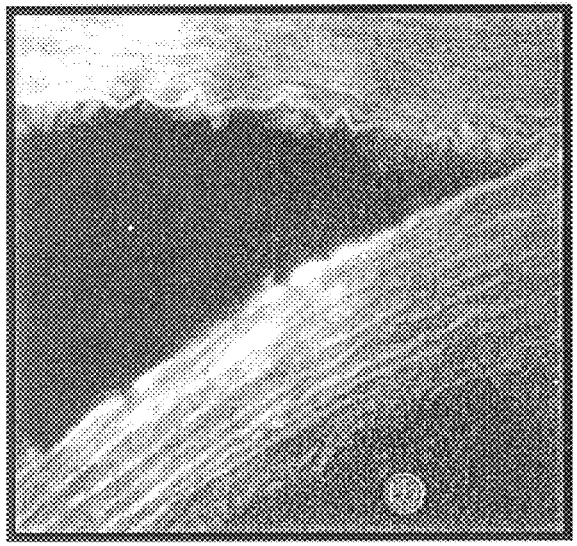
FIG. 4 shows confocal microscopy fluorescent images of rabbit arteries after heparin treatment. 4L2 shows left artery with pulse; 4R2 shows right artery no pulse; 4L1 shows left artery with pulse; and 1L3 shows left artery no pulse.
Figure 4B:
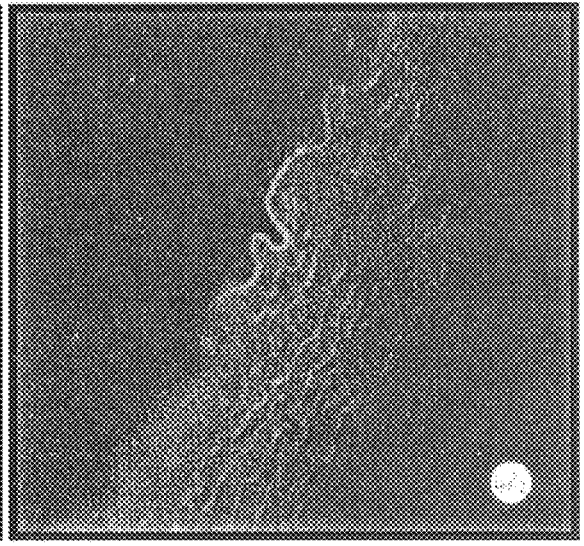
Figure 4C:
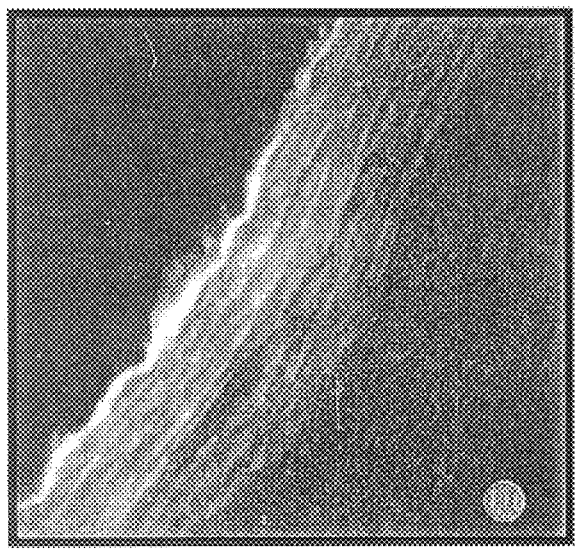
Figure 4D:
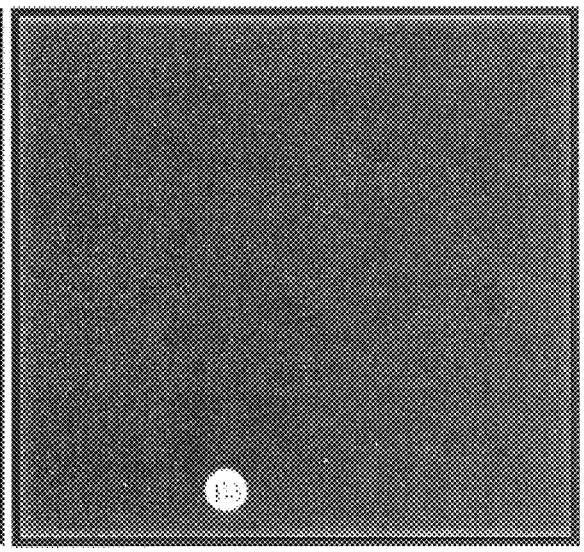
Figure 5A:
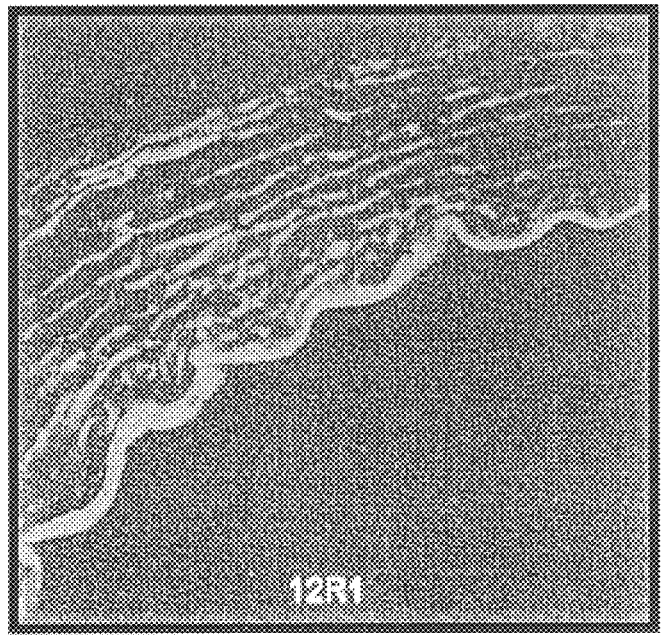
FIG. 5 shows confocal microscopy fluorescent images of rabbit arteries after heparin treatment. 12R1, right artery with pulse and 12L1, left artery, no pulse.
Figure 5B:
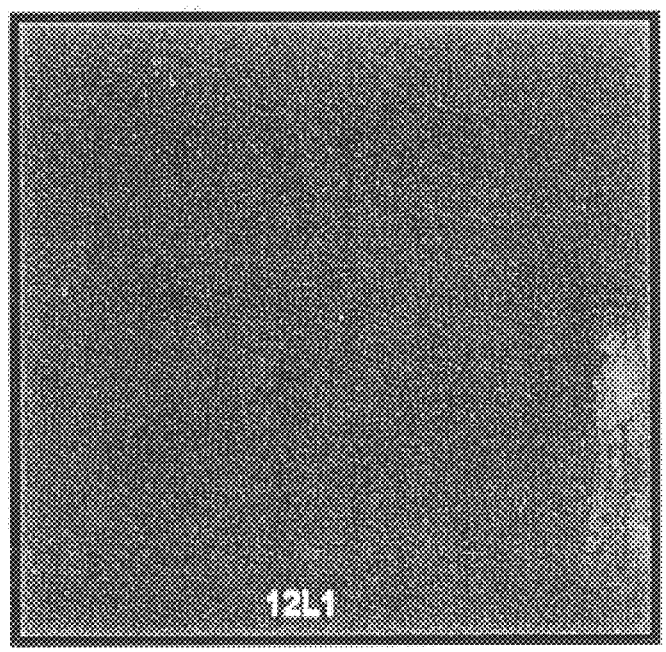

The present invention provides a method for the local, controlled, and sustained intravascular delivery of a therapeutic composition to a vessel in a subject using electroporation techniques. The method utilizes pulsed electric fields and has an advantage of allowing lower concentrations of compositions to be utilized as opposed to high dosages typically used with passive delivery modalities.

The method of the invention provides a delivery system that allows controlled sustained, high local concentrations of pharmacologic agents to be delivered directly at a site without exposing the entire circulation to the agent. Pharmacologic approaches to inhibit smooth muscle cells migration and proliferation, for example, have been effectively used at supraphysiological doses in animal research studies. However, such high concentrations may be impractical for clinical use in humans because of the risk of systemic side effects and the lack of specific targeting of drugs given systemically at such high dosages. This invention is clinically relevant for the local treatment of arteries undergoing catheter-based interventions, such as angioplasty, atherectomy, rotablating or stenting, for example.

In a preferred embodiment, the invention provides a method for sustained intravascular delivery of a composition to a subject. The method includes administering the composition to the subject and applying an electrical impulse to a vessel via electroporation, wherein the impulse is of sufficient strength and time for the impulse to cause electroporation of at least one cell in the interior of the vessel such that the composition is delivered into the cells in the vessel and is retained in the vessel thereby resulting in sustained delivery. In one aspect of the invention, iontophoresis can be employed to further deliver the composition to a cell, either prior to, simultaneously with or after electroporation.

The term "sustained" as used herein means that once the composition is delivered to the vessel, it is retained in the vessel for a period of time of as long as 24 to about 36 hours, and typically for 12 hours. In other words, there is no appreciable washout of the composition as compared with the concentration of the composition delivered under conventional delivery (e.g., passive diffusion or IO).

The terms "intravascular" and "vessel" mean any artery, vein or other "lumen" in the subject's body to which the electric pulse can be applied and to which the composition can be delivered. A lumen is known in the art as a channel within a tube or tubular organ. Examples of preferred vessels in the method of the invention include the coronary artery, carotid artery, the femoral artery, and the iliac artery. While not wanting to be bound by a particular theory, it is believed that the electric impulse applied to the vessel allows the delivery of the composition primarily to the cells of the medial region of the vessel, but also to the intima and less so to the adventitia.

The composition delivered by the method of the invention includes any composition which would have a desired biological effect at the site of electroporation. For example, preferred compositions include antithrombotic, antirestenoitic, antiplatelet, and antiproliferative compositions. Other compositions include platelet receptor and mediator inhibitors, smooth muscle cell proliferation inhibitors, growth factor inhibitors, GpIIb/IIIa antagonists, agents that inhibit cell adhesion and aggregation, agents that block thromboxane receptors, agents that block the fibrinogen receptor, etc. Specific examples of such compositions include heparin (including high and low molecular weight and fragments thereof), hirulog, tissue plasminogen activator (tPA), urokinase, streptokinase, warfarin, hirudin, angiotensin converting enzyme (ACE) inhibitors, PDGF-antibodies, proteases such as elastase and collagenase, serotonin, prostaglandins, vasoconstrictors, vasodialators, angiogenesis factors, Factor VIII or Factor IX, TNF, tissue factor, VLA-4, growth-arrest homeobox gene, gax, L-arginine, GR32191, sulotroban, ketanserin, fish oil, enoxaprin, cilazapril, forinopril, lovastatin, angiopeptin, cyclosporin A, steroids, trapidil, colchicine, DMSO, retinoids, thrombin inhibitors, antibodies to von Willebrand factor, antibodies to glycoprotein IIb/IIIa, calcium chelation agents, etc. Other therapeutic agents (e.g., those used in gene therapy, chemotherapeutic agents, nucleic acids (e.g., polynucleotides including antisense, for example c-myc and c-myb), peptides and polypeptides, including antibodies) may also be administered by the method of the invention.

The therapeutic composition can be administered alone or in combination with each other or with another agent. Such agents include combinations of tPA, urokinase, prourokinase, heparin, and streptokinase, for example. Administration of heparin with tissue plasminogen activator would reduce the dose of tissue plasminogen activator that would be required, thereby reducing the risk of clot formation which is often associated with the conclusion of tissue plasminogen activator and other thrombolytic or fibrinolytic therapies.

Compositions used in the method of the invention include biologically functional analogues of the compositions described herein. For example, such modifications include addition or removal of sulfate groups, addition of phosphate groups and addition of hydrophobic groups such as aliphatic or aromatic aglycones. Modifications of heparin, for example, include the addition of non-heparin saccharide residues such as sialic acid, galactose, fucose, glucose, and xylose. When heparin is used as the composition, it may include a fragment of naturally occurring heparin or heparin-like molecule such as heparan sulfate or other glycosaminoglycans, or may be synthetic fragments. The synthetic fragments could be modified in saccharide linkage in order to produce more effective blockers of selectin binding. Methods for producing such saccharides will be known by those of skill in the art (see for example: M. Petitou, Chemical Synthesis of Heparin, in Heparin, Chemical and Biological Properties, Clinical Applications, 1989, CRC Press Boca Raton, Fla. D. A. Lane and V. Lindahl, eds. pp. 65–79).

The composition administered by the method of the invention may be a mixture of one or more compositions, e.g., heparin and tPA. Further, compositions such as heparin may include a mixture of molecules containing from about 2 to about 50 saccharide units or may be homogeneous fragments as long as the number of saccharide units is 2 or more, but not greater than about 50.

Where a disorder is associated with the expression of a gene (e.g., IGF-1, endothelial cell growth factor), nucleic acid sequences that interfere with the gene's expression at the translational level can be delivered. This approach utilizes, for example, antisense nucleic acid, ribozymes, or triplex agents to block transcription or translation of a specific mRNA, either by masking that mRNA with an antisense nucleic acid or triplex agent, or by cleaving it with a ribozyme.

Preferably the subject is a human, however, it is envisioned that the method of sustained in vivo delivery of compositions via electroporation as described herein can be performed on any animal.

Preferably, the therapeutic composition is administered either prior to or substantially contemporaneously with the electroporation treatment. The term "substantially contemporaneously" means that the therapeutic composition and the electroporation treatment are administered reasonably close together with respect to time. The chemical composition of the agent will dictate the most appropriate time to administer the agent in relation to the administration of the electric pulse. The composition can be administered at any interval, depending upon such factors, for example, as the nature of the clinical situation, the condition of the patient, the size and chemical characteristics of the composition and half-life of the composition.

The composition administered in the method of the invention can be administered parenterally by injection or by gradual perfusion over time. The composition can be administered intravenously, intraperitoneally, intramuscularly, subcutaneously, intracavity, or transdermally, and preferably is administered intravascularly at or near the site of electroporation.

Preparations for administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Further, vasoconstrictor agents can be used to keep the therapeutic composition localized prior to pulsing.

Figure 6:
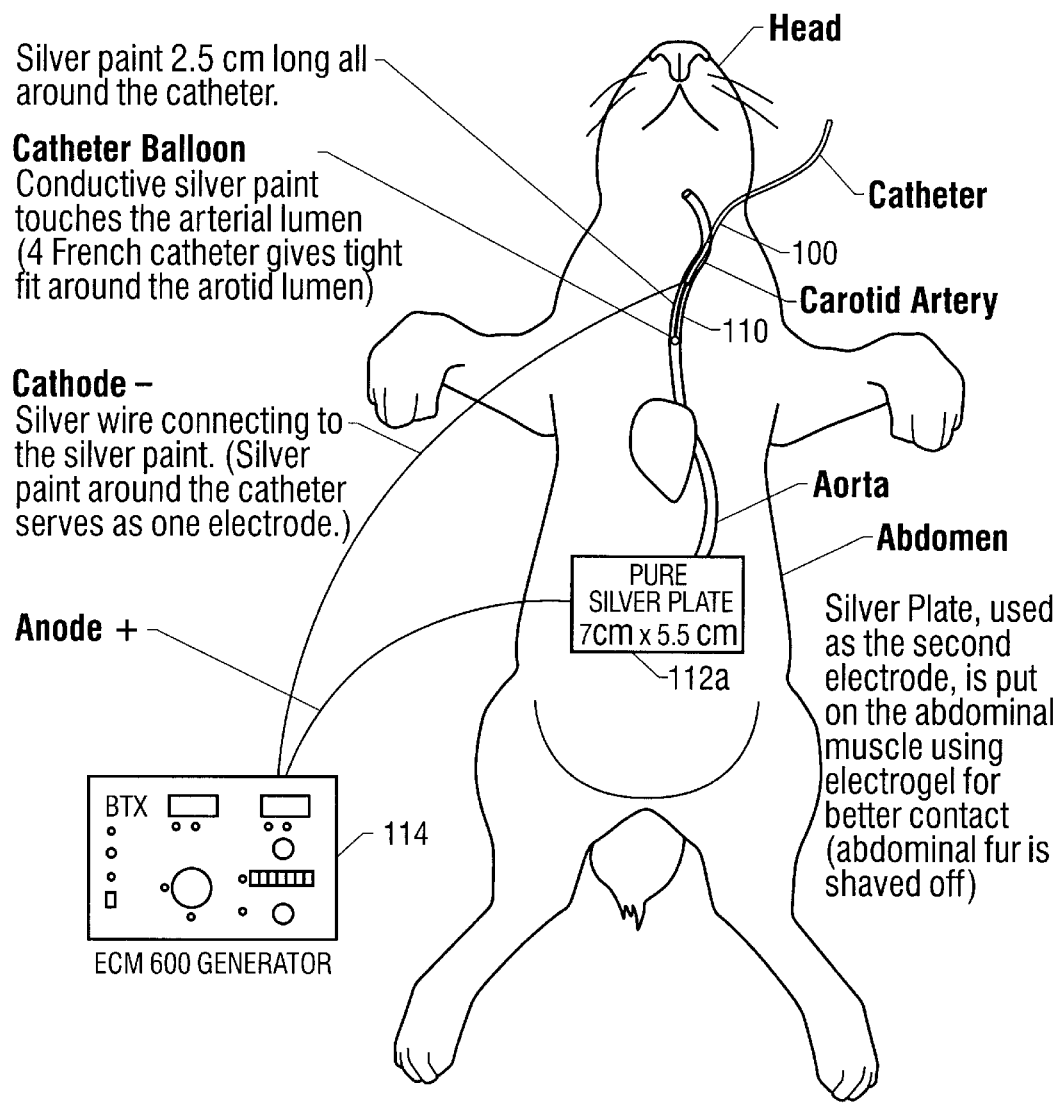
FIG. 6 is a schematic diagram of a rabbit treated by the method of the invention, including the catheter description.
Figure 7:
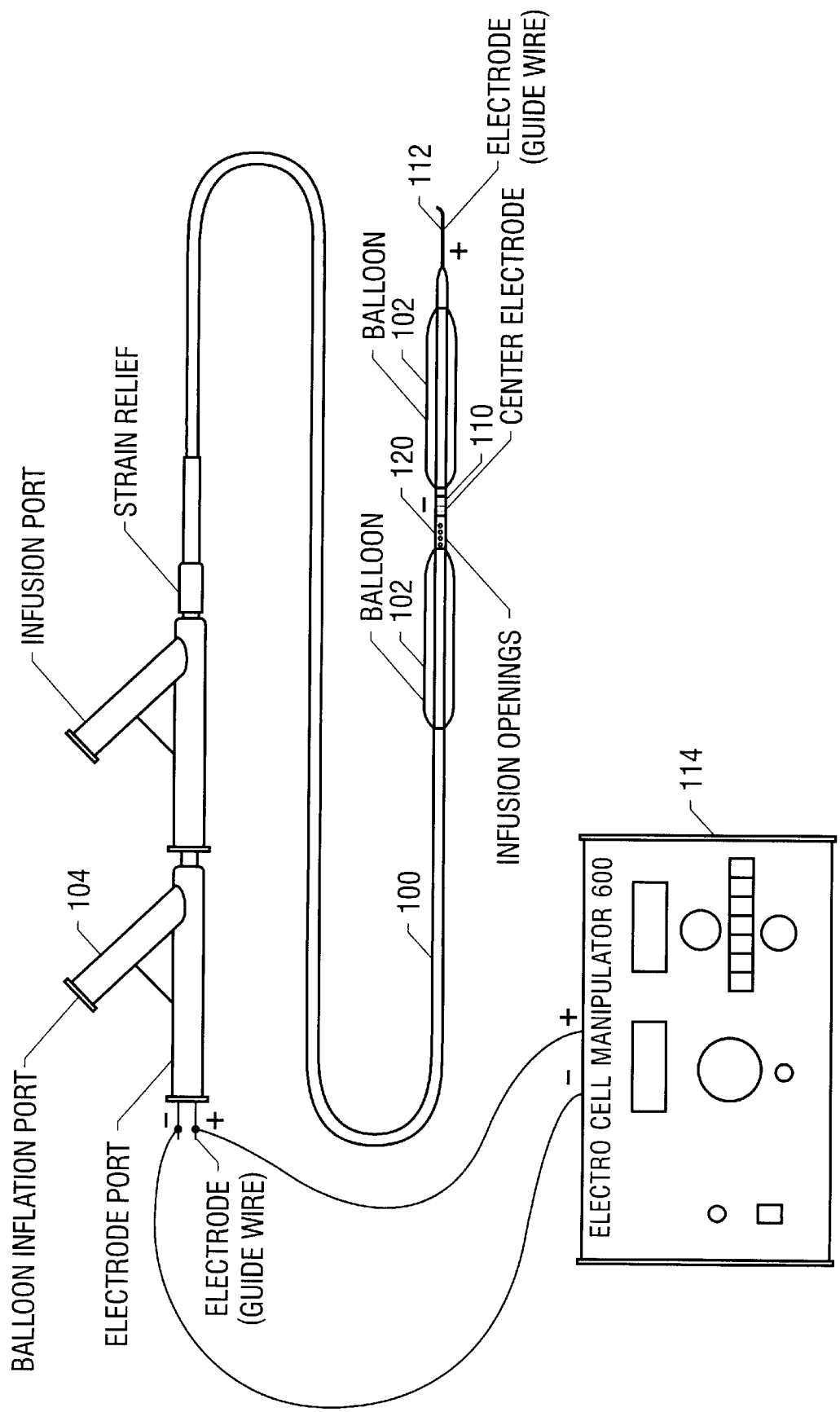
FIG. 7 is a schematic diagram of an exemplary endoluminal electroporation catheter of the invention.

In another embodiment, the invention provides a catheter device 100 useful in the method of the invention that can be modified as described herein, as shown in FIGS. 1, 6, and 7. The catheter may be, for example, a modified Berman catheter (Arrow International, Inc., Reading, Pa.). One of skill in the art will know of other balloon catheter devices for endoluminal electroporation mediated drug delivery that can be modified according to the present invention.

The catheter 100 may include at least one inflatable balloon 102 near the distal end of the catheter 100, and at least one inflation port 104 for inflating each balloon 102, in a conventional manner. The catheter 100 also includes a first electrode 110 and a second electrode 112 that are coupled by wires to a voltage source generator 114, which may be, for example, an ECM 600 exponential generator from BTX, a division of Genetronics, Inc., San Diego, Calif. The first electrode 110 is preferably placed close to at least one infusion opening 120. In one embodiment, the infusion openings 120 may be coincident with the first electrode 110, such that the first electrode 110 completely surrounds at least one infusion opening 120.

The first electrode 110 is preferably made of an electrically conductive material that is biologically compatible, e.g., biologically inert, with a subject. Examples of such material include silver or platinum wire wrapped around or laid on or near the surface of the catheter 100; a plated or painted coating of conductive material, such as silver paint, on some portion of the catheter 100; or a region of the catheter 100 that has been made conductive by implantation (during or after manufacture, such as by ion implantation) of electrically conductive materials, such as powdered metal or conductive fibers. The conductor need not be limited to metal, but can be a semiconductor or conductive plastic or ceramic. For ease of manufacture, the embodiments illustrated in FIGS. 6 and 7 use conductive silver paint for the first electrode 110 as a coating on approximately 2.5 cm of the length of the catheter 100 near the infusion ports 120.

The second electrode 112 similarly comprises an electrically conductive material, and can be of the same or different type of conductive material as the first electrode 110. In the embodiment shown in FIG. 6, the second electrode comprises a silver plate 112a configured to be applied to a portion of the body of a subject such that an electric field sufficient to cause electroporation of at least one cell in a vessel is generated when voltage from the voltage source 114 is applied to the first electrode 110 and the second electrode 112. The second electrode, when placed externally, is preferably placed on bare skin (e.g., shaved abdominal muscle of the subject), preferably using a conductive gel for better contact. FIG. 7 shows that the second electrode 112 may be a conductive guide wire for the catheter 100.

The first electrode 110 and the second electrode 112 are coupled to the voltage source 114 by conductors, which may be, for example, silver or platinum wires, but can be any conductive structure, such as flexible conductive ink within the catheter 100 for connecting the first electrode 110.

The infusion ports 120 can be made during or after manufacture of the catheter 100, and can be placed on one or both sides of the first electrode 110, or within the bounds of the first electrode 110.

In an alternative embodiment, the second electrode 112 may be formed in a manner similar to the first electrode 110 and positioned between the first electrode 110 and the infusion openings 120, or positioned with the infusion openings 120 between the first electrode 110 and the second electrode 112. Other configurations of the first electrode 110 and the second electrode 112 can be utilized, such as interdigitated electrodes with infusion openings 120 nearby or between the interdigitated "fingers" of the electrodes, or as concentric rings with the infusion openings within the centermost ring, between the centermost and outermost ring, and/or outside of the outermost ring. Additional configurations are within the scope of the present invention so long as they provide a structure that, when supplied by voltage from the voltage source 114, generates an electric field sufficient to cause electroporation of at least one cell in the vessel.

In operation, the catheter 100 is positioned so that a balloon 102 traverses or crosses a stenotic lesion, for example, and the balloon 102 is inflated to expand the vessel (e.g., an artery or vein), thereby dilating the lumen of the vessel. A therapeutic composition is delivered into the vessel via the infusion openings 120, and at least during part of the time before, during, or after infusion occurs, electrical pulses from the voltage source 114 are applied to the first electrode 110 and second electrode 112 so as to cause electroporation of at least one cell in the vessel. Following delivery of the therapeutic composition to such cell, the catheter may be withdrawn, unless additional composition delivery and electroporation is desired.

The methods described above are also applicable with metallic stents. The stent itself forms one set of electrodes while a guide wire acts as the second electrode. Stents, on their own, or coated with heparin, are useful for reduction of restenosis. Such results can be further augmented when combined with pulsed electric fields. This would be particularly suitable for angioplasty where a stent is deployed. (For detailed review, see de Jaegere, P. P. et al., *Restenosis Summit Proc. VIII*, 1996, pp 82–109). Stent implantation, along with local delivery of antirestenotic drugs by pulsed electric fields reduces the restenosis rate. Besides a normal stent, a retractable or biodegradable stent can also be used with this mode of delivery.

In another aspect of the invention, the described method is useful for bypass grafts. These can include aortocoronary, aortoiliac, aortorenal, femoropopliteal. In the case of a graft with autologous or heterologous tissue, the cells in the tissue can be electroporated, ex vivo, with a nucleic acid encoding a protein of interest. Since electroporation is relatively fast, a desired nucleic acid can be transferred in a saphenous vein, e.g., outside the body, while the extracorporeal circulation in the patient is maintained by a heart-lung machine, and the vein subsequently grafted by standard methods. Where synthetic material is used as a graft, it can serve as a scaffolding where appropriate cells containing a nucleic acid sequence of interest that has been electroporated, ex vivo, can be seeded.

The method of the invention can be used to treat disorders by delivery of any composition, e.g., drug or gene with a catheter, as described herein. For example, patients with peripheral arterial disease, e.g., critical limb ischemia (Isner, J. M. et al, Restenosis SummitVIII, Cleveland, Ohio, 1996, pp 208–289) can be treated as described herein. Both viral and non-viral means of gene delivery can be achieved using the method of the invention. These include delivery of naked DNA, DNA-liposome complex, ultraviolet inactivated HVJ (haematoagglutanating virus of Japan) liposome vector, delivery by particle gun (e.g., biolistics) where the DNA is coated to inert beads, etc. Various nucleic acid sequences encoding a protein of interest can be used for treatment of cardiovascular disorders, for example. The expression of the growth factors PDGF-B, FGF-1 and TGFβ1 has been associated with intimal hyperplasia, therefore, it may be desirable to either elevate (deliver sense constructs) or decrease (deliver antisense) such gene expression. For example, whereas PDGF-B is associated with smooth muscle cell (SMC) proliferation and migration, FGF-1 stimulates angiogenesis and TGF β1 accelerates procollagen synthesis.

Any composition that inhibits SMC proliferation and migration, platelet aggregation and extracellular modeling is also desirable for use in the electroporation-mediated delivery method of the invention. Such compositions include interferon-γ which inhibits proliferation and expression of α-smooth muscle actin in arterial SMCs and non-protein mediators such as prostaglandin of the E series.

Examples of other genes to be delivered by the method of the invention includes Vascular endothelial growth factor (VEGF) and endothelial specific mitogen, which can stimulate angiogenesis and regulate both physiologic and pathologic angiogenesis.

Administration of the composition in the method of the invention may be used for ameliorating post-reperfusion injury, for example. When treating arterial thrombosis, induction of reperfusion by clot lysing agents such as tissue plasminogen activator (tPA) is often associated with tissue damage.

Administration of the composition by the method of the invention, alone or in combination with other compositions, for example that may be administered passively, is useful in various clinical situations. These include but are not limited to: 1) acute arterial thrombotic occlusion including coronary, cerebral or peripheral arteries; 2) acute thrombotic occlusion or restenosis after angioplasty; 3) reocclusion or restenosis after thrombolytic therapy (e.g., in an ishemic tissue); 4) vascular graft occlusion; 5) hemodialysis; 6) cardiopulmonary bypass surgery; 7) left ventricular cardiac assist device; 8) total artificial heart and left ventricular assist devices; 9) septic shock; and 10) other arterial thromboses (e.g., thrombosis or thromboembolism where current therapeutic measures are either contraindicated or not effective).

The method of the invention is also useful for the treatment of microbial infections. Many microbes, such as bacteria, rickettsia, various parasites, and viruses, bind to vascular endothelium and leukocytes. Thus, the method of the invention may be used to administer a composition to a patient to prevent binding of a microbe which uses a particular receptor (e.g., selectin) as its binding target molecule, thereby modulating the course of the microbial infection.

The method of the invention can be used to treat vasculitis by administering to a patient a composition described above. Tissue damage associated with focal adhesion of leukocytes to the endothelial lining of blood vessels is inhibited by blocking the P- and L-selectin receptors, for example.

The dosage ranges for the administration of the compositions in the method of the invention are those large enough to produce the desired effect in which the symptoms of the disease/injury are ameliorated. The dosage should not be so large as to cause adverse side effects. Generally, the dosage will vary with the age, condition, sex and extent of the disease in the patient and can be determined by one of skill in the art. The dosage can be adjusted by the individual physician in the event of any complication. When used for the treatment of inflammation, post-reperfusion injury, microbial/viral infection, or vasculitis, or inhibition of the metastatic spread of tumor cells, for example, the therapeutic composition may be administered at a dosage which can vary from about 1 mg/kg to about 1000 mg/kg, preferably about 1 mg/kg to about 50 mg/kg, in one or more dose administrations.

Controlled delivery may be achieved by selecting appropriate macromolecules, for example, polyesters, polyamino acids, polyvinyl pyrrolidone, ethylenevinylacetate, methylcellulose, carboxymethylcellulose, protamine sulfate, or lactide/glycolide copolymers. The rate of release of the therapeutic composition may be controlled by altering the concentration of the macromolecule.

Another method for controlling the duration of action comprises incorporating the composition into particles of a polymeric substance such as polyesters, polyamino acids, hydrogels, polylactide/glycolide copolymers, or ethylenevinylacetate copolymers. Alternatively, it is possible to entrap the composition in microcapsules prepared, for example, by coacervation techniques or by interfacial polymerization, for example, by the use of hydroxymethylcellulose or gelatin-microcapsules or poly(methylmethacrolate) microcapsules, respectively, or in a colloid drug delivery system. Colloidal dispersion systems include macromolecule complexes, nanocapsules, microspheres, beads, and lipid-based systems including oil-in-water emulsions, micelles, mixed micelles, and liposomes.

The various parameters including electric field strengths required for the electroporation of any known cell is generally available from the many research papers reporting on the subject, as well as from a database maintained by Genetronics, Inc., San Diego, Calif., assignee of the subject application. The electric fields needed for in vivo cell electroporation are similar in amplitude to the fields required for cells in vitro. These are in the range of from 100 V/cm to several kV/cm. This has been verified by the inventors own experiments and those of others reported in scientific publications.

Pulse generators for carrying out the procedures described herein are and have been available on the market for a number of years. One suitable signal generator is the ELECTRO CELL MANIPULATOR Model ECM 600 commercially available from BTX, a division of Genetronics, Inc., of San Diego, Calif., U.S.A. The ECM 600 signal generator generates a pulse from the complete discharge of a capacitor which results in an exponentially decaying waveform. The electric signal generated by this signal generator is characterized by a fast rise time and an exponential tail. In the ECM 600 signal generator, the electroporation pulse length is set by selecting one often timing resistors marked R1 through R10. They are active in both High Voltage Mode (HVM) (capacitance fixed at fifty microfarads) and Low Voltage Mode (LVM) (with a capacitance range from 25 to 3,175 microfarads).

The application of an electrical field across the cell membrane results in the creation of transient pores which are critical to the eletroporation process. The ECM 600 signal generator provides the voltage (in kV) that travels across the gap (in cm) between the electrodes. This potential difference defines what is called the electric field strength where E equals kV/cm. Each cell has its own critical field strength for optimum electroporation. This is due to cell size, membrane make-up and individual characteristics of the cell wall itself. For example, mammalian cells typically require between 0.5 and 5.0 kV/cm before cell death and/or electroporation occurs. Generally, the required field strength varies inversely with the size of the cell.

The ECM 600 signal generator has a control knob that permits the adjustment of the amplitude of the set charging voltage applied to the internal capacitors from 50 to 500 volts in LVM and from 0.05 to 2.5 kV in the HVM. The maximum amplitude of the electrical signal is shown on a display incorporated into the ECM 600 signal generator. This device further includes a plurality of push button switches for controlling pulse length, in the LVM mode, by a simultaneous combination of resistors parallel to the output and a bank of seven selectable additive capacitors.

The ECM 600 signal generator also includes a single automatic charge and pulse push button. This button may be depressed to initiate both charging of the internal capacitors to the set voltage and to deliver a pulse to the outside electrodes in an automatic cycle that takes less than five seconds. The manual button may be sequentially pressed to repeatedly apply the predetermined electric field.

The waveforms of the voltage pulse provided by the generator in the power pack can be an exponentially decaying pulse, a square pulse, a unipolar oscillating pulse train or a bipolar oscillating pulse train, for example. Preferably, the waveform used for the method of the invention is an exponential pulse. The voltage applied between the at least first and second electrode is sufficient to cause electroporation of the vessel such the composition delivered to the vessel is retained for a period of time, as described above. The field strength is calculated by dividing the voltage by the distance (calculated for 1 cm separation; expressed in cm) between the electrodes. For example, if the voltage is 500 V between two electrode faces which is ½ cm apart, then the field strength is 500/(½) or 1000 V/cm or 1 kV/cm. Preferably, the amount of voltage applied between the electrodes is in the range of about 10 volts to 200 volts, and preferably from about 50 to 90 volts.

The pulse length can be 100 microseconds ($\mu s$) to 100 millisecond (ms) and preferably from about 500 $\mu s$ to 10 ms. There can be from about 1 to 10 pulses applied to an area or group of cells. The waveform, electric field strength and pulse duration are dependent upon the exact construction of the catheter device and types of molecules in the composition to be transferred to the cells or vessel via electroporation. One of skill in the art would readily be able to determine the appropriate pulse length and number of pulses.

The following examples are intended to illustrate but not limit the invention. While they are typical of those that might be used, other procedures known to those skilled in the art may alternatively be used.

EXAMPLE 1

ENDOLUMINAL INJECTION OF FLUORESCEINATED HEPARIN AND PULSED ELECTRICAL STIMULATION OF THE CAROTID ARTERY IN A SPONTANEOUSLY BREATHING RABBIT

1. Methods

Experiments were performed in 12 New Zealand white rabbits of either sex (2.5–3.4 kg) preanesthetized with xylazine (2 mg.kg$^{-1}$) and ketamine (50 mg.kg$^{-1}$) intramuscularly and an injection of alphachloralose (30 mg.kg$^{-1}$) intraveneously through an ear vein. A supplemental dose of 10 mg.kg$^{-1}$ chloralose was given every hour. The anesthetic state was maintained such that the toe-pinching reflex and corneal reflexes were absent.

All experiments were conducted in accordance with the guidelines adopted by American Physiological Society on the use of animals for research.

Animals were placed supine and strapped on the surgical table. The trachea was intubated to allow spontaneous breathing of ambient air. Electrocardiogram (EKG) of the animal was obtained by using Lead II in differential mode. End-tidal $CO_2$ tension was monitored by a $CO_2$ analyzer (Datex, Puritan-Bennett). Body temperature was kept at the 38–38.5° C. range by radiant heating.

2. Surgical Preparation and Experimental Protocol

A longitudinal incision in the cervical region was made in the rabbit to expose the common carotid arteries on both sides. Approximately 6 cm in length of carotid artery on each side was isolated from the surrounding tissue and vagosympathetic nerve trunk. The caudal end of the carotid artery on one side was transiently occluded with a vascular clip at the junction between the neck and chest. A small incision was then made at the rostral end of the artery just below transversus vein) to push an electroporator catheter (FIG. 1) through this incision. After insertion of the catheter, the catheter balloon was repeatedly inflated for 30 seconds inside the arterial lumen in order to denude the endothelial lining. An indelible ink mark was placed on the inflated portion of the artery. The balloon was then deflated and the catheter tip was held just above the vascular clip.

A 0.2 ml of freshly prepared diluted heparin (1 mg. of fluoresceinated heparin (F-heparin) with an activity of 167 unit/mg [Molecular Probe, Inc.] dissolved in 4 ml) was injected through the one port of a double lumen catheter over a period of about 10 seconds. The catheter was then pulled out of the artery and the vascular clip was taken off from the caudal end to restore blood flow in the artery. Exactly the same procedure was adopted for the contralateral carotid artery (test artery). The only exception was that for the test artery, the carotid artery was stimulated intraluminally using a platinum or silver electrode. Two platinum or silver wires were coiled around the catheter just above the balloon for a length of about 10 mm with an interelectrode distance of 2 mm–3 mm.

Lead II EKG was differentially amplified and the output was continuously monitored on an osciloscope (Tektronix) and recorded on a Gould TA-2000 thermal-array recorder for evaluation. 1–12 hours after heparin injection, both carotid arteries were excised and immediately flash frozen in isopentane pre-chilled in liquid nitrogen. Arteries were stored in $-70°$ C. until further processing.

Arterial segments were subsequently freeze sectioned (10 micron) transversely. Microscopic slides containing arterial sections were observed under a Zeiss confocal laser (argon-krypton) scan microscope (LSM 410 Invert), (excitation at 495 nm and emission at 515 nm) to obtain video image (magnification 40 times) of fluorescence. Subsequently, control and test samples were compared by analyzing fluorescence intensity by Line Intensity Scan at different depths of the arterial wall using commercially obtained software (Image 1:Universal Imaging Corp.).

3. Protocols of Pulsed Stimulation

The luminal wall of the carotid artery was stimulated through bipolar platinum or silver electrodes, which were laid against the luminal surface sufficiently without damage. Pulsed activation of the luminal surface was obtained using an exponential pulse generator (Model ECM 600, BTX, a division of Genetronics, Inc., San Diego, Calif.). Four pulses of 50–60 V amplitude with a pulse width of ~500 $\mu s$ were applied over a period of 60 seconds. This protocol was adopted either for the left or right carotid artery.

4. Observation and Data Analysis

During pulse stimulation of the carotid artery, mild twitching of the cervical region could be seen, but no appreciable change was observed in EKG dynamics over the entire experimental duration.

Green fluorescence heparin of the arterial wall could be distinctly seen in the microscopic slide preparations (in different layers of the arterial wall). Confocal scan image of the arterial wall showed penetration of F-heparin in both control and test samples. However, it was evident that the flourescent-intensity in the test sample was much stronger and went into the deeper region of the arterial wall (FIGS. 2–5).

The pulsed electrical stimulation facilitated introduction of small amount (~50 ug) of F-heparin effectively to the deeper region of arterial wall in a physiologically normal experimental animal. Heparin was mostly present in the media but also in the intima of the vessel wall. However, the intensity dropped significantly towards the adventitia. It is possible that only the portion of the electrode making contact with the luminal wall shows more fluorescence than the adjacent space. From the tissue sectioning, it is not possible to say which portion of the tissue sectioning of the luminal wall sample had contact with the electrodes. However, it is possible that if some sections in the test sample show greater penetration and intensity than the others, those sections probably were in contact with the luminal wall. Also, the fluorescent image could not ascertain if balloon inflation of the bilateral arteries had equal degree of endothelial denudation, the variation in which could alter the penetration of F-heparin among the samples.

FIG. 1 shows a schematic of the catheter used in the above examples. One of the problems of working with fluoresceinated heparin is that there is considerable amount of autofluorescence from the collagen and elastin of the tissue sample. In absolute terms of fluorescent intensity, these tend to distort the real pattern of the fluorescence in the vessel wall due to heparin alone. However, in the present examples, in every case, it is clear that the relative fluorescent intensity was always stronger in the treated vessel that was pulsed compared to the non-pulsed artery. All the photographs had identical magnification (40×) and the brightness and contrast were set to the same level for photography (FIGS. 2–5). All epifluorescence images were monitored in Sony videocon monitor attached to a Hamamatsu CCD camera.

However, by processing the samples at higher pH (9.0), it was possible to considerably reduce or even eliminate the interfering autofluorescence. The photos of FIGS. 2–5 indicated that the local delivery of heparin in the vessel completely washes out in two hours, whereas heparin delivery in the pulsed artery was sustained for at least 12 hours.

EXAMPLE 2

FIG. 6 shows another configuration for a catheter useful in the method of the invention, whereby conductive silver paint or a similar conductive material is placed around the catheter covering a length of approximately 2.5 cm. This portion of the catheter is attached to a silver wire which, in turn, is connected to one terminal of a generator, e.g., ECM 600 exponential generator (BTX, a division of Genetronics, Inc., San Diego, Calif.). The second electrode is placed externally and is placed on the abdominal muscle, preferably using a gel for better contact (FIG. 6, shaved area). This second electrode, serving as the anode, is in turn connected to the other terminal of the generator.

Figure 8A:
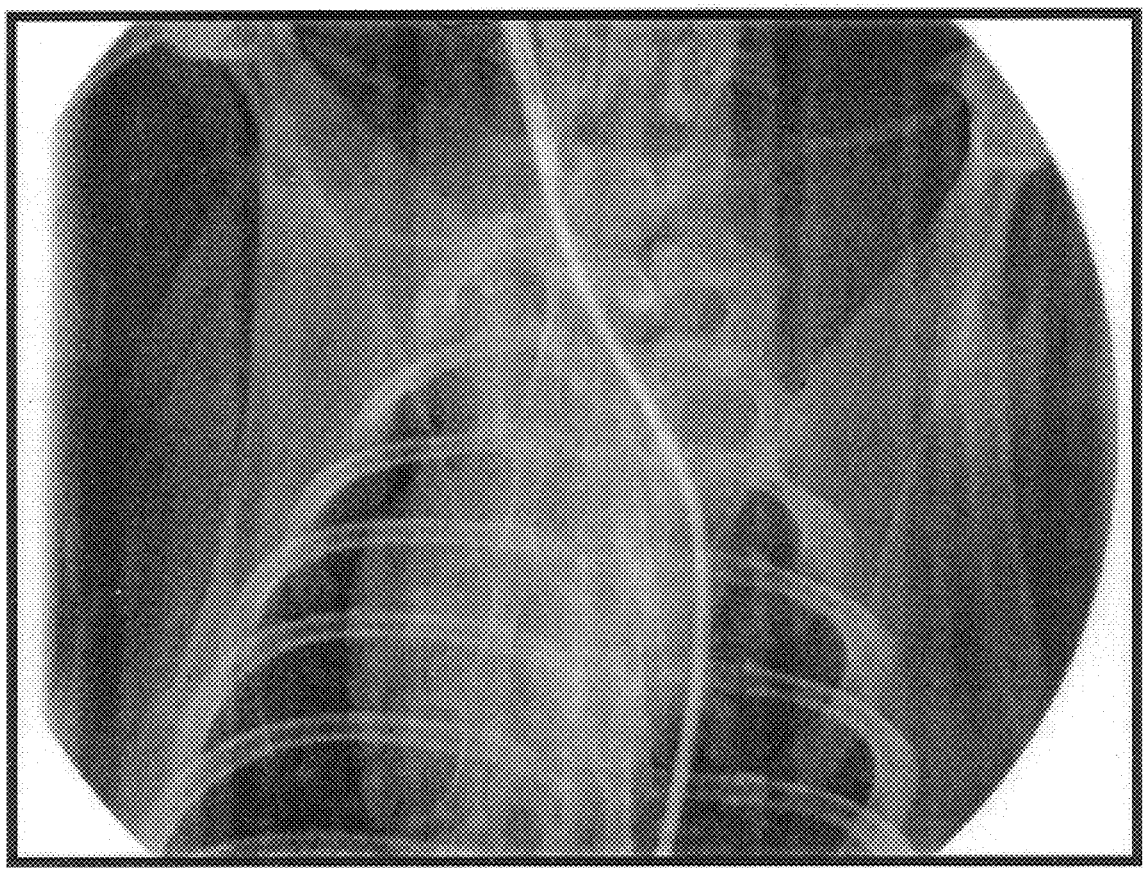
FIG. 8, panels a–c, show x-rays of insertion of the catheter into the carotid artery (a), infusion of radiocontrast dye (b), and balloon inflation (c), respectively.
Figure 8B:
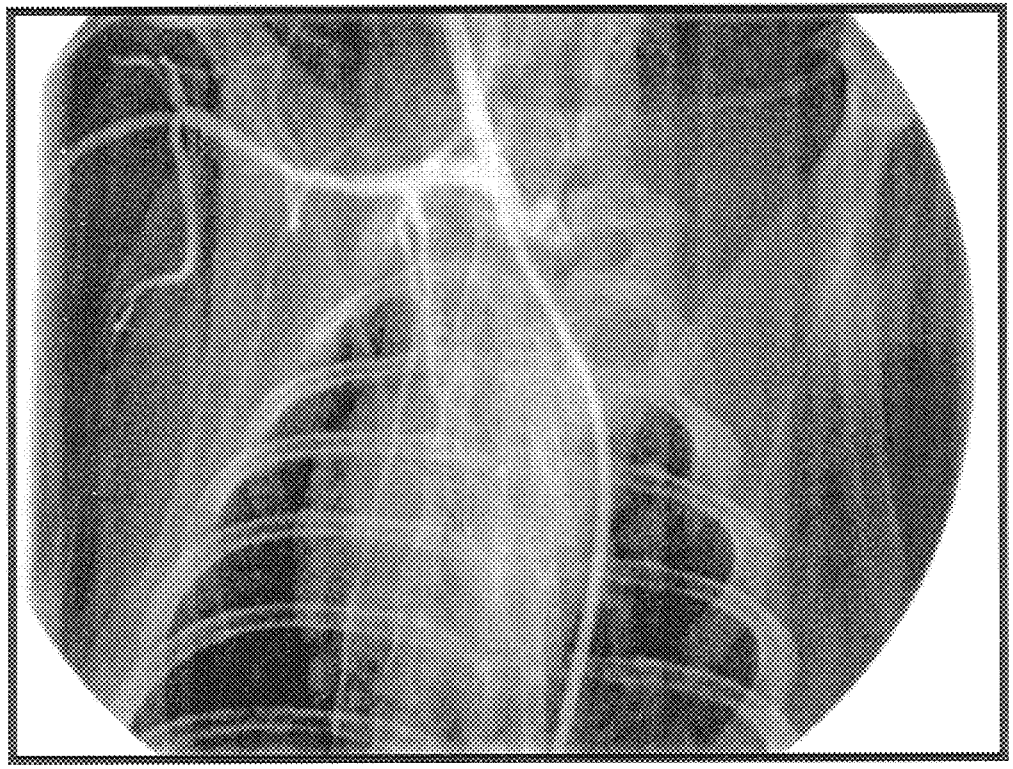
Figure 8C:
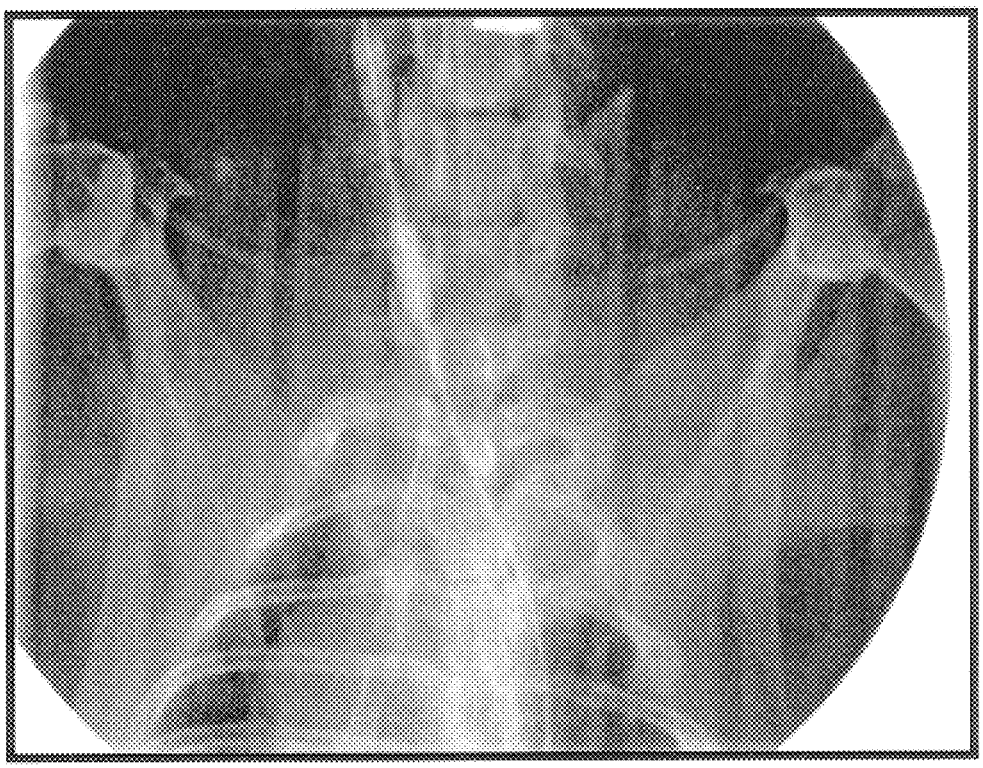

Another embodiment of the catheter comprises one electrode positioned between two balloons and a guidewire acting as a second catheter. Such a configuration is shown in FIG. 7. This catheter was used in the following experiment. Three rabbits weighing ~4 Kg were anesthetized with xylazine (0.1 ml/kg) and ketamine (0.5 ml/kg i.m.). General anesthesia was maintained with α-chloralose (30 mg/Kg. i.v.). Intubation was endotracheal, as described in example 1. A femoral artery in the leg on one side of the rabbit was exposed. A 5F sheath was introduced and the catheter was pushed under fluoroscopic guidance to the right or left carotid artery. A series of x-rays, FIG. 8, panels a–c, show successful deployment of the catheter (panel a, insertion). Radiocontrast fluid was infused (panel b) allowing confirmation of the catheter position, the patient artery, the balloon and the built-in radiopaque marker, as well as presence of the dye in the side branches. After balloon inflation, (panel c) 1 ml of fluoresceinated heparin (concentration 1 mg dissolved in 2 ml: biological activity of heparin as per manufacturer: 167 U) was infused between the occluded segment via the drug port and the artery pulsed immediately with the balloons in the inflated condition. Initially, field parameters tested were ~60 V and four pulses each of ~600 $\mu$s pulse length. With these settings, very little uptake of heparin was observed in the treated artery. In a subsequent experiment, voltage and pulse length were changed to 57 V and 22 ms, respectively. As before, four pulses were delivered from ECM 600 pulse exponential generator. The balloon was deflated immediately afterwards with the catheter taken out, but the sheath was left behind to avoid bleeding from the nicked femoral artery. Two hours after infusion of F-heparin, both arteries (treated and the contralateral untreated artery) were taken out for processing. Microscopic images of the treated artery showed massive uptake of the heparin. The fluorescent image of the artery was extremely intense, and the separated arterial sections could not be discerned. Although the control artery also shows fluorescence, visually it was much weaker. Although heparin was not delivered into the control artery, it is obvious that there was systemic circulation from infusion of heparin in the treated artery- part of which must have been taken up by the control artery. In addition, fluorescence due to collagen and elastin was also present. However, both autofluorescence correction at higher pH, as described previously, and computer subtraction of the fluorescence from the control artery from that of the treated artery, showed deep penetration and uptake of the F-heparin in the pulsed artery.

A similar catheter (as depicted in FIG. 7) was also used for a gene marking experiment in a rabbit carotid artery. A New Zealand white rabbit weighing 3.5 Kg was anesthetized with ketamine/xylene cocktail (IM). Intubation was with halothane @1%. After a midline incision, the right common carotid was isolated with silk ligature. 5F sheath was placed into right common carotid over the guidewire after an initial scissor nick in artery. 014" Schneider guidewire was placed through the sheath into the left iliac artery. The electroporation (EP) catheter was advanced over the wire to left iliac artery. 50% contrast injections with the balloon inflated through the infusion port guided placement to avoid side branches. The infusion sleeve was flushed with saline and the balloons inflated 2 atom. Plasmid (150 $\mu$l) (a standard marker gene, lacZ, driven by a CMV promoter) was injected into the infusion port followed by saline. The iliac was pulsed from a BTX ECM 600 exponential pulse generator. Three pulses were given at approximately 10 sec intervals at 76 V and 758 $\mu$s.

For the control artery, balloons were deflated and the wire placed down the right iliac. The procedure was as described above, except that no pulse was applied. The dwell time was ~30 secs. After the procedure, the balloons were deflated and catheters and wires removed. The carotid was ligated proximal and distal to the entry site and the incision was closed in 2 layers. 1500 units of heparin were given after the sheath was in place.

The plasmid DNA was electroporated into the rabbit iliac artery (catheter was guided through to the iliac via the carotid as described above) and gene expression was confined five days later using standard x-gal processing of the artery. In contrast, the control artery did not show detectable gene expression.

EXAMPLE 3

For further drug delivery studies, the same protocol will be followed as described in detail in Example 1. Forty New Zealand white rabbits will be used for these studies. Time points of approximately 2 hours and 24 hours (group 1) will be tested with balloon catheters as described herein.

Twenty animals, ten animals in each of the time points of group 1, will be used. Both the left and the right arteries will serve as the treated (T) and the control (C). These will be chosen randomly but the number for the T and C will be the same. An ECM 600 pulse generator, which delivers exponential pulses and was used to generate the results described above, will also be used for these experiments.

Ten animals will be tested with square wave pulses from a BTX T820 Square Wave Pulser and arteries will be excised after two hours for subsequent studies. The arteries which will serve as T and C will be randomized. BTX T820 delivers square wave pulses where the number of pulses, the voltage and the pulse length can be adjusted. The voltage is about 60 V and the pulse parameters are: four pulses delivered at 1 Hz each of 40 ms (based on studies with the BTX T820 on rat vascular smooth muscle cell experiments in vitro). Square wave pulses have been known to be gentler to some cells. In this group, there will be five arteries in each of the treated and control category. The inflammatory response of the vessel due to balloon inflation as well as application of the pulsed electric field is also evaluated.

Twenty rabbits will be used where the catheter will be introduced either percutaneously or via a small incision in the femoral. This would give results on twenty treated and twenty control arteries. Arteries will be processed after eight hours. The ECM 600 will be used to deliver exponential pulses. An endoluminal balloon catheter used herein has one electrode between two balloons whereas the guide wire will serve as the second electrode (one design). To facilitate proper viewing of the balloons in the inflated and the deflated position under fluoroscopic guidance, radio-opaque markers will be put in appropriate positions. Calculations suggest that there will be enough field penetration into the arteries to deliver drugs although the electrodes are not in direct contact with the arteries.

For each of the specific aims given above, electric field plots will be generated using a commercially available software package EMP (Field Precision, Albuquerque, N. Mex.). This package solves Poisson's equation is solved numerically by finite elements methods. The initial parameters are electrode geometry, resistivities of the artery from the lumen side and the connective tissue side and the range of field strength to be investigated.

The amount of heparin left in the vessel will be determined in each case following a procedure recommended by Molecular Probe. An InSpeck Microscope Image Intensity Calibration Kit will be used. First, the microscope will be calibrated with the beads (microsphere) provided in the kit and the fluorescein-heparin solution will be equilibrated to the 100% microsphere. Alternatively, for different size microsphere, the available figures for "fluorescein equivalent per microsphere" can be used.

The protocol for reduction of autofluorescence due to collagen and elastin from the arterial wall of the isolated rabbit carotid artery is as follows: Tris-buffered glycerol is prepared (90 ml glycerol and 5 ml of 0.5M Tris-HCl, pH 9.0). This is dispensed in 19 ml aliquots in glass scintillation vials and stored 4° C. 2% n-propyl gallate (npg: anti-fading substance) is prepared in tris-buffer (2 mg npg and 1.0 ml of 0.5M tris-HCl, pH 9.0) is prepared fresh and protected from light. 1 ml of the 2% npg solution is added to 19 ml of tris-buffered glycerol and the solution is protected from light. This is the solution used to mount arterial sections on to the microscopic glass slides. Precaution needs to be taken that the solution is discarded on discoloration. All images will be obtained at 40× magnification under immersion oil (Plan-Neofluor objective). Identical brightness and contrast will be set for all photographs.

Although the invention has been described with reference to the presently preferred embodiment, it should be understood that various modifications can be made without departing from the spirit of the invention. Accordingly, the invention is limited only by the following claims.

What is claimed is:

1. A method for sustained intravascular delivery of a composition to cells of a vessel in a subject, the method comprising:

denuding the endothelial lining of a vessel, administering the composition locally to the vessel in the subject;

applying an electrical impulse directly to cells of the vessel via electroporation by directly contacting the vessel with electrodes, wherein the impulse is of sufficient strength and time for the impulse to cause electroporation of at least one cell in the interior of the vessel such that the composition is delivered into the vessel and is retained in the vessel for sustained, localized delivery.

2. The method of claim 1, wherein the composition is selected from the group consisting of an antithrombotic, antirestenoitic, antiplatelet, platelet receptor and mediator inhibitor, growth factor inhibitor, antibody, antiinflammatory and antiproliferative composition.

3. The method of claim 1, wherein the composition is selected from the group consisting of heparin, hirulog, tPA, urokinase, streptokinase, cyclosporin, antistatin, and warfarin.

4. The method of claim 1, wherein the electrical impulse applied is from approximately 50 to 90 volts.

5. The method of claim 1, wherein the electrical impulse applied has a duration of about 100 $\mu$s to 100 ms.

6. The method of claim 5, wherein the electrical impulse applied has a duration of from about 100 $\mu$s to 1000 $\mu$s.

7. The method of claim 1, wherein the administering of the composition and the application of the electrical impulse are substantially contemporaneous.

8. The method of claim 1, wherein application of the electrical impulse is via a catheter apparatus.

9. The method of claim 1, wherein the electrical impulse (s) is selected from the group consisting of square wave pulses, exponential waves, unipolar oscillating wave forms of limited duration, bipolar oscillating wave forms of limited duration, and other wave forms generating electric fields.

10. The method of claim 1, wherein the electrical impulse has a pulsing frequency of about 1 to 100 Hz.

11. The method of claim 1, wherein from about 1 to 10 electrical pulses are applied.

12. The method of claim 1, further comprising using iontophoresis for delivery of the composition to the cell.

13. The method of claim 1, wherein the vessel is a blood vessel.

14. The method of claim 1, wherein said cell in the interior of the vessel is in the adventitial region of the vessel.

15. A method for sustained intravascular delivery of a composition to cells of a vessel in a subject, the method comprising: denuding the endothelial lining of a vessel administering the composition to the vessel of a subject using an apparatus having:

a catheter having at least one inflatable balloon portion;

at least one infusion passage for introducing the composition into the subject;

a first electrode positioned adjacent to at least one infusion passage;

a second electrode positioned with respect to the first electrode and the subject such that an electric field sufficient to cause electroporation of at least one cell in the vessel is generated, thereby allowing the composition to enter at least one cell after introduction of the composition through at least one infusion passage;

applying an electrical impulse to cells of a vessel in the subject via electroporation, wherein the electrodes are in the vessel and wherein the impulse is of sufficient strength and time for the impulse to cause electroporation of at least one cell in the interior of the vessel such that the composition is delivered locally into the vessel and is retained in the vessel for sustained delivery.

16. The method of claim 1, wherein said cell in the interior of the vessel is in the medial region of the vessel.

17. The method of claim 1 or claim 15, wherein the composition is a polynucleotide.

18. The method of claim 17, wherein the polynucleotide encodes a polypeptide selected from the group consisting of Vascular endothelial growth factor (VEGF), endothelial specific mitogen, platelet derived growth factor, fibroblast growth factor, and interferon.

* * * * *